(12) United States Patent
Cappello

(10) Patent No.: US 7,473,427 B2
(45) Date of Patent: Jan. 6, 2009

(54) BLUE-GREEN ALGAE COMPOSITION

(75) Inventor: John V. Cappello, Myrtle Beach, SC (US)

(73) Assignee: Cappellos, Inc., King of Prussia, PA (US)

( * ) Notice: Subject to any disclaimer, the term of this patent is extended or adjusted under 35 U.S.C. 154(b) by 0 days.

(21) Appl. No.: 11/788,693

(22) Filed: Apr. 19, 2007

(65) Prior Publication Data

US 2008/0260881 A1    Oct. 23, 2008

(51) Int. Cl.
*A61K 36/02* (2006.01)

(52) U.S. Cl. .................................. 424/195.17

(58) Field of Classification Search .................. None
See application file for complete search history.

(56) References Cited

OTHER PUBLICATIONS

Aphanin website (http://web.archive.org/web/20060224095219/http://www.bluegreenfoods.com/aphanin_facts.htm—web archived version from Feb. 2006).*
Crystal Manna website (http://web.archive.org/web/20060327073946/http://www.ancientsuninc.com/crystalmanna.html—web archived version from Mar. 2006).*
Phycomin website (http://web.archive.org/web/20060224095053/http://www.bluegreenfoods.com/phycomin_facts.htm—web archived version from Feb. 2006).*
Desert Lake Technologies, LLc, P.O. Box 489, Klamath Falls, OR 97601 www.desertlake.com,, Aphanin A Novel COX-2 Inhibitor, product specification sheet, date unknown, two pages, accessed Mar. 30, 2007.
Desert Lake Technologies, LLc, P.O. Box 489, Klamath Falls, OR 97601 www.desertlake.com,, Phycomin Ingredient For The Mind, product specification sheet, date unknown, two pages, accessed Mar. 30, 2007.
Ancient Sun Nutrition, P.O. Box 7555, Ashville, NC 28802, www.ancientsuninc.com, product descriptions, date unknown, Crystal Manna Whole AFA, one page, accessed Mar. 31, 2007.
Amazon.com, 1200 12th Ave. Suite 1200, Seattle, WA 98144, www.amazon.com/120-Ct-Blue-Manna-Capsules/dp/B000E1U8848, Blue Manna Capsules, date unknown, one page, accessed Mar. 31, 2007.

* cited by examiner

*Primary Examiner*—Susan C Hoffman
(74) *Attorney, Agent, or Firm*—Lawrence J. Shurupoff

(57) ABSTRACT

A broad spectrum functional food formulation based on blue-green algae and concentrated extracts of blue-green algae provides numerous health benefits when orally administered in therapeutically effective amounts. Whole aphanizomenon flos-aqua is combined with concentrates of phycocyanin and phenylethylamine to provide a life-enhancing dietary supplement which can stimulate stem cell production, elevate mood and reduce inflammation and joint pain.

5 Claims, No Drawings

BLUE-GREEN ALGAE COMPOSITION

FIELD OF DISCLOSURE

The present disclosure relates to life-enhancing compositions which include blue-green algae and supplemental extracts thereof.

BACKGROUND

Blue-green algae forms the life-supporting foundation of the natural food chain by providing the essential vitamins, minerals, proteins, and nutrients required to support life. Blue-green algae has long been used as a dietary supplement for promoting and sustaining human health.

One form of blue-green algae known as aphanizomenon flos-aqua (AFA) is currently under study for its ability to stimulate stem cell production. A link between AFA and stem cell production is disclosed in U.S. Pat. No. 6,814,961 and is incorporated herein by reference. Stem cells not only combat disease, they also contribute to health maintenance and reduce the effects of injury and aging.

AFA is available in the form of a dried blue-green powder naturally containing eighteen amino acids and twelve vitamins essential for human health. A representative breakdown of AFA includes about 60% proteins, 24% carbohydrates, 5% minerals, 5% lipids, 4% water, 1% chlorophyll, and 1% fiber.

SUMMARY

It has been found that the health-promoting effects of blue-green algae can be significantly improved by supplementing blue-green algae with concentrated amounts of extracts derived from blue-green algae. For example, it has been found that a particularly effective health-promoting formulation can be produced by adding supplemental amounts of phycocyanin and phenylethylamine (PEA) to whole blue-green algae.

Phycocyanin is the blue-green pigment present in blue-green algae such as AFA. Phycocyanin stores protein in algae cells and serves as an antioxidant. It has been shown that phycocyanin can inhibit the production of prostaglandins by inhibiting cyclooxygenase-2. This can reduce or prevent inflammation such as caused by injury, by arthritis, or by irritants.

PEA is also found in blue-green algae such as AFA. In humans, PEA is produced in the brain during periods of elevated moods such as happiness and joy. PEA easily crosses the blood-brain barrier and enhances dopamine and norepinephrine transmission. These neurotransmitters can produce elevated moods and reduce depression. PEA, an endogenous neurotransmitter, is also believed to promote alertness and excitement, and can be effective in treating attention deficit disorders.

Both PEA and phycocyanin can be extracted from whole AFA by centrifuging, filtering and other well known extraction and sizing techniques. Both are blue-green in color and available in powder form.

Although PEA and phycocyanin are present in blue-green algae such as AFA, their concentrations are relatively low. Accordingly, their beneficial effect on human health requires ingesting unrealistically large quantities of algae in order to obtain sufficient amounts of PEA and phycocyanin to elevate mood, reduce inflammation and provide the additional health benefits noted above.

By supplementing blue-green algae, such as AFA, with concentrated amounts of PEA and phycocyanin, the beneficial effects of each component can be realized within realistic convenient dosages. The addition of concentrated extracts of AFA facilitates the inclusion of therapeutically effective amounts of all three components, namely whole blue-green algae (AFA), PEA and phycocyanin in a single easy-to-swallow capsule. One need only ingest one or two standard size capsules to conveniently achieve the full benefit of each ingredient.

An added benefit of combining whole blue-green algae with PEA and phycocyanin is improved transport of PEA and phycocyanin into the bloodstream after ingestion. That is, polysaccharides, which are present in whole AFA, aid in transporting both PEA and phycocyanin through the digestive tract and into the blood. This is important not only from a simple efficiency perspective, but also from an economic perspective.

Because PEA and phycocyanin occur naturally in blue-green algae in relatively small amounts, large amounts of blue-green algae must be processed to extract PEA and phycocyanin. This makes the PEA and phycocyanin extracts very expensive. By improving the transport of PEA and phycocyanin into the bloodstream by combining them with whole AFA, smaller amounts of these components are required to be ingested in order to produce therapeutic effects. This results in a significant cost savings and convenience in oral administration.

It can be appreciated that the combination of whole blue-green algae (AFA), PEA and phycocyanin can be particularly beneficial to those in middle age and older who commonly suffer from joint pain and depression. These and other conditions can be effectively treated with the blue-green algae formulation noted above and described in further detail below.

DESCRIPTION OF THE EMBODIMENTS

In accordance with one embodiment, whole green-blue algae, such as sun-dried powdered aphanizomenon flos-aqua (AFA), is combined with supplemental therapeutic amounts of phenylethylamine (PEA) and phycocyanin to provide a broad spectrum functional food formulation. This formulation can be effective in improving one's health and general quality of life.

For example, daily doses of whole AFA in the amount of at least about 500 mg are considered at the lower end of being therapeutically effective. As used throughout herein, the term "about" means plus or minus ten percent. Preferably, at least about 1000 mg per day of whole AFA should be taken to achieve therapeutically effective life-enhancing results. These results include increased production of stem cells and all benefits which derive from increased stem cell production.

As a supplement to whole AFA, daily doses of PEA in the amount of at least about 0.35 mg are considered at the lower end of being therapeutically effective. Preferably, at least about 0.7 to 1.1 mg per day of PEA should be taken to achieve life-enhancing results. These results include increased attention and elevated moods. Larger amounts of PEA can be taken, up to about 10 mg per day, although such amounts can become excessively costly for an over-the-counter product.

As an additional supplement to whole AFA, daily doses of phycocyanin in the amount of at least about 25 mg are considered at the lower end of being therapeutically effective. Preferably, at least about 50 mg per day of phycocyanin should be taken to achieve life-enhancing results. These results include the reduction and elimination of inflammation and joint pain such as caused by arthritis.

Obtaining pure PEA and phycocyanin is difficult and extremely expensive. However, commercially-available extracts of blue-green algae (AFA) contain elevated concentrations of these components in combination with other components of AFA. These extracts can be used effectively in place of the pure form of AFA and phycocyanin to provide therapeutically effective amounts of PEA and phycocyanin at reasonable cost without any loss of efficacy.

For example, PEA is commercially available in concentrated form and is sold as a powder under the brand Phycomin. This product contains on average about 8 to 11 mg of PEA per gram. This extract and is centrifugally extracted from whole AFA using known techniques. Ingesting 50 mg of Phycomin extract will provide about 0.4 to 0.55 mg of PEA.

Phycocyanin is also available commercially in a concentrated form sold under the brand Aphanin. This product contains about 25% by weight of phycocyanin and is centrafugally extracted from whole AFA. Ingesting 200 mg of Aphanin extract will provide about 50 mg of phycocyanin.

One formulation found effective is based on a combination of whole green-blue algae (AFA), Phycomin extract and Aphanin extract. This formulation can be provided in the form of an oral vegetable-based capsule containing a total of 750 mg of the three component formulation. Preferably, two capsules are taken together or one capsule is taken in the morning and one capsule is taken in the evening for a total daily dosage of 1.5 gram.

Each oral capsule can contain about 500 mg of whole AFA, about 200 mg of Aphanin extract and about 50 mg of Phycomin extract. This formulation ensures a dosage per capsule of about 50 mg of phycocyanin provided by the Aphanin extract and about 0.4 mg of PEA provided by the Phycomin extract. Taking two capsules per day doubles this dosage to about 1 gram of AFA, about 100 mg of phycocyanin and about 0.8 mg of PEA. This has been found to be a preferred daily dosage.

Amounts of each component can vary widely by increasing the amounts of phycocyanin and PEA over those nominal amounts stated. However, such increased amounts of PEA and phycocyanin can become cost prohibitive. The amounts of each component can be reduced in half so as to allow for smaller and easier-to-swallow capsules containing about 250 mf of whole green-blue algae (APA), about 100 mg of Aphanin extract and about about 25 mg of Phycomin extract. In this case, four capsules can be ingested daily for achieving therapeutically effective results.

AFA, phycocyanin and PEA are each water soluble and together provide all 18 amino acids comprising the human body's basic building blocks, as well as all major minerals and more than 50 trace minerals. This formulation also provides at least 12 key vitamins, unsaturated fatty acids, natural anti-oxidants and natural neuro-modulating ingredients. All of the above act together to facilitate and enhance the human body's ability to repair and maintain itself using components derived from AFA, a whole food produced naturally in nature to sustain and perpetuate life.

There has been disclosed heretofore the best embodiment of the disclosure presently contemplated. Obviously, numerous modifications and variations of the present disclosure are possible in light of the above teachings. It is therefore to be understood that within the scope of the appended claims, the disclosure may be practiced otherwise than as specifically described herein.

What is claimed is:

1. A dietary supplement administered orally, comprising:
    at least about 250 mg of whole blue-green algae, said whole blue-green algae comprising polysaccharides;
    at least about 25 mg of phycocyanin;
    at least about 0.35 mg of phenylethylamine; and
    wherein said polysacchardes in said whole blue-green algae aid in transporting said phycocyanin and said phenylethylamine through a digestive tract and into a blood stream.

2. The dietary supplement of claim 1, wherein said whole blue-green algae comprises aphanizomenon flos-aqua.

3. The dietary supplement of claim 1, wherein said phycocyanin and said phenylethylamine comprise extracts of whole blue-green algae.

4. The dietary supplement of claim 1, wherein said whole blue-green algae, said phycocyanin and said phenylethylamine are provided in powder form and encapsulated in a gelatin capsule.

5. The dietary supplement of claim 1, wherein said amount of whole blue-green algae comprises about 250 mg to 500 mg of whole aphanizomenon flos-aqua, said amount of phycocyanin comprises about 25 to 50 mg of phycocyanin and said amount of phenylethylamine comprises about 0.35 mg to 0.70 mg of phenylethylanine, and wherein said supplement is provided in an oral capsule.

* * * * *